US007197771B2

(12) United States Patent
Hollander

(10) Patent No.: US 7,197,771 B2
(45) Date of Patent: *Apr. 3, 2007

(54) GARMENT FOR PREVENTING MUSCLE STRAIN

(76) Inventor: Scott Hollander, 18411 Hatteras St., Apt. 232, Tarzana, CA (US) 91356

( * ) Notice: Subject to any disclaimer, the term of this patent is extended or adjusted under 35 U.S.C. 154(b) by 104 days.

This patent is subject to a terminal disclaimer.

(21) Appl. No.: 10/938,433

(22) Filed: Sep. 10, 2004

(65) Prior Publication Data
US 2006/0053524 A1  Mar. 16, 2006

Related U.S. Application Data

(63) Continuation of application No. 10/189,364, filed on Jun. 27, 2002, now Pat. No. 6,817,032.

(51) Int. Cl.
*A41D 13/00* (2006.01)
(52) U.S. Cl. ............................................................ 2/69
(58) Field of Classification Search ..................... 2/16, 2/69, 456, 114, 115, 125, 127, 93, 94, 910, 2/917; 128/878, 879; 602/5, 18, 20, 21, 602/60, 61, 64; 482/44, 45, 92, 131
See application file for complete search history.

(56) References Cited

U.S. PATENT DOCUMENTS

| 2,750,940 | A | 6/1956 | Fear |
| 3,554,194 | A | 1/1971 | Johnson |
| 4,100,620 | A | 7/1978 | Pecoraro |
| 4,198,964 | A | 4/1980 | Honneffer |
| 4,327,909 | A | 5/1982 | Neufeld |
| 4,382,302 | A | 5/1983 | Watson |
| 4,572,172 | A | 2/1986 | Williams |
| 4,601,285 | A | 7/1986 | Whitchurch |
| 4,658,442 | A | 4/1987 | Tomlinson et al. |
| 4,733,658 | A | 3/1988 | Ruthven, Jr. |
| 4,747,779 | A | 5/1988 | Gerstung |
| 4,966,136 | A | 10/1990 | Bates |

(Continued)

OTHER PUBLICATIONS 1 page of photos of items sold by Royce Medical Corporation, Camarillo, CA (www.roycemedical.com).

(Continued)

*Primary Examiner*—Tejash Patel
(74) *Attorney, Agent, or Firm*—Knobbe Martens Olson & Bear LLP

(57) ABSTRACT

A garment adapted for wear by persons desiring to maintain their arms in a fixed position along their upper body. The garment includes an upper portion, such as a shirt, adapted for wear on the upper body, and at least one hand portion, such as a glove. The shirt is preferably made of a loop material and the glove includes a region of hook material. Utilizing the loop and hook materials, the glove can be releasably attached to the shirt to maintain the user's hand in a fixed position along the user's upper body. The garment is primarily intended for maintaining one or both of the user's arms close against the body to facilitate relaxation while in cramped or tight positions, such as in an airplane seat. However, the garment may also be used in a wide variety of applications wherein it is desired to support one or both of the user's arms in a releasably fixed position.

11 Claims, 7 Drawing Sheets

U.S. PATENT DOCUMENTS

| | | |
|---|---|---|
| 5,465,425 A | 11/1995 | Crispin |
| 5,688,137 A | 11/1997 | Bustance |
| 5,692,239 A | 12/1997 | Lewis |
| 5,957,873 A | 9/1999 | Allen |
| 6,041,436 A | 3/2000 | Keen |
| 6,079,049 A * | 6/2000 | Moir ............................... 2/69 |
| 6,182,291 B1 | 2/2001 | Garvey |
| 6,526,591 B2 | 3/2003 | Leumi |
| 6,595,936 B1 | 7/2003 | Oladipo |
| 6,817,032 B2 * | 11/2004 | Hollander ........................ 2/69 |
| 6,974,429 B2 * | 12/2005 | Moore et al. ................... 602/4 |
| 7,037,281 B1 * | 5/2006 | Jeffrey et al. .................. 602/4 |

OTHER PUBLICATIONS 3 pages of photos of items sold by BoneGuard Inc., Randolph, MA (www.boneguard.com).

* cited by examiner

GARMENT FOR PREVENTING MUSCLE STRAIN

RELATED U.S. APPLICATION DATA

This application is a continuation of U.S. patent application Ser. No. 10/189,364, issued Jun. 27, 2002 as U.S. Pat. No. 6,817,032.

BACKGROUND OF THE INVENTION

1. Field of the Invention

The present invention relates to a garment, and more specifically to a garment adapted for assisting a person to releasably secure one or both hands to his or her upper body.

2. Description of the Related Art

Various devices have been proposed for wear on a body to assist a person in maintaining his or her arms or legs in a desired position. For example, U.S. Pat. No. 5,688,137 to Bustance describes an athletic training device adapted to be worn by a boxer to help maintain the boxer's arms in the desired "ready" position during training exercises. The device in Bustance includes a vest element worn around the torso and a pair of sleeve elements worn around the bicep region of each arm. The vest and sleeve elements each include attachment means for releasably attaching the sleeves to the vest. This device improves the boxer's form by training him to hold his upper arms tightly against the sides of his torso while in the defensive position.

In another example, U.S. Pat. No. 4,747,779 to Gerstung describes a form-keeping device for training gymnasts or spring-board divers to hold their legs and feet together during a gymnastic exercise or a dive. The device in Gerstung comprises a pair of straps adapted to be worn around the ankles and a pair of spacing elements configured to maintain the ankles at a fixed distance apart. Each of the ankle straps includes a portion having a loop or hook material for releasably attaching the two straps together during use to keep the ankles together during the desired routine.

In yet another example, U.S. Pat. No. 4,625,334 to Proffer describes a harness adapted for wear by the front rider of a tandem pair on a motorcycle. The harness is provided with a number of handholds for enabling the rear rider to hold on to the front rider. The handholds are positioned on the garment such that the rear rider can comfortably maintain his or her arms around the waist of the front rider.

Although various garment-type devices have been proposed for assisting persons to maintain their arms or legs in desired positions during physical activities, none of the proposed devices provides a means for assisting persons to releasably secure their hands to a desired location along their upper body. Such a device is very desirable for a number of reasons.

For example, larger individuals are often quite uncomfortable during travel, such as by airplane, bus or train, because seats on these vehicles are typically not well-suited for larger body sizes and cannot be adjusted in width. As a result, the arms of larger individuals tend to extend over the armrest and thereby contact adjacent passengers. Worse yet, an individual's arm may extend into an aisle where it can be hit and injured by passersby or food carts.

To avoid contacting other passengers and objects, some individuals have found it helpful to cross their arms and lay their hands flatly against their chest with their palms facing their torso. This position effectively narrows the individual's body width and thereby helps to prevent the problems just described. However, this position is difficult or impossible to maintain for extended periods due to the resulting muscle strain on the individual's shoulders and arms. The muscle strain and the associated discomfort can make it difficult or impossible for the passenger to relax or sleep during travel. Moreover, it has been found that prolonged muscle strain can lead to long-term health problems, such as, for example, tendinitis.

Another situation where it would be desirable for a person to maintain one or both hands along his or her upper body is after an injury. Following an injury to an arm or shoulder, a sling is typically used to immobilize the arm. However, in many situations, a conventional sling may be uncomfortable, cumbersome or impractical. Furthermore, during the latter stages of the healing process, it may be desirable to use an injured arm for limited purposes; however, it can be very cumbersome to take off and put on a sling each time the person wishes to use his or her arm.

Another situation where it would be desirable for a person to maintain one or both hands along the upper body is during transportation of a victim via a stretcher or similar means. Many stretchers do not include a strap or belt for securing the victim onto the stretcher. Other times, a victim is unable or unwilling to accept being secured to a stretcher via a strap. When no strap is used, it is difficult to prevent the victim's arms from falling over the sides of the stretcher, particularly if the victim is particularly large or the stretcher is narrow. If one or both of the victim's arms fall over the sides of the stretcher it can seriously aggravate an existing injury or result in an additional injury.

Another situation where it would be desirable for a person to maintain one or both hands along the upper body is for minimizing the effects of certain neurological disorders. Some types of neurological disorders may be outwardly manifested by conditions such as body tremors or involuntary muscular movements. At times, such as in certain social situations or for safety concerns, it would be desirable to provide a device to help stabilize the person's hands and/or arms to prevent involuntary movements of the hands and/or arms.

Thus, for at least these reasons, there remains a very real and substantial need for a new and improved garment that can be used to releasably secure a user's hands to the upper body in a desired position, such as in a folded configuration. Such a garment would be beneficial for the reasons described above and would be particularly useful for allowing larger individuals to travel in greater comfort. To be practical, it is desirable that such a garment be comfortable to wear. It is also desirable that such a garment has a minimum number of parts and utilizes simple attachment means for convenience and ease of use. It is also desirable that such a garment is constructed of durable materials that can be washed and reused. Finally, it is desirable that such a garment be inexpensive to manufacture, aesthetically appealing, and versatile enough for a wide range of applications. The present invention addresses these needs.

SUMMARY OF THE INVENTION

A primary object of the present invention is to provide a garment that enables a person to releasably secure one or both hands to his or her upper body.

In one aspect, the garment comprises an upper portion, such as a vest or shirt, adapted for wear on the user's torso region. The upper portion has at least a region formed with a first attachment means. The garment also comprises a hand portion, such as a glove or strap, adapted for wear along at least one of the user's hands. The hand portion has a region formed with a second attachment means that is releasably engageable to the first attachment means for attaching the user's hands to his or her upper body.

In another aspect, a variety of attachment means can be used with the present invention including, but not limited to, loop and hook materials, buttons, hooks, snaps and clasps.

In another aspect, the upper portion of the garment is in the form of a strap that can be worn around the user's neck. The first attachment means is preferably located along the ends of the strap. The strap may include a padded region along the portion of the strap that passes along the back of the user's neck. The padded region increases the user's comfort and can be used to support the user's head during rest.

In another aspect, the upper portion of the garment comprises a shoulder strap or a chest strap having a section with the first attachment means disposed along the outer surface of the strap. The hand portion, such as a glove, is releasably engageable to the strap for immobilizing one or both hands or arms. The embodiment using the shoulder strap is particularly well-suited for immobilizing an injured arm during rehabilitation. This embodiment has numerous advantages over a conventional sling, such as, for example, the arm can be easily detached or reattached to the strap as needed and the arm can be attached at a selectable location along the strap to increase comfort.

In another aspect, a method of manufacturing the garment is provided. In one preferred embodiment, the method generally comprises providing an upper portion adapted for wear on the torso region of the user's body, the upper portion being formed of a loop material that is adapted to be releasably engageable with a hook material. The method also comprises providing a hand portion adapted for wear on at least one of the user's hands and attaching a portion of the hook material along the palm side of the hand portion.

Other features and advantages of the invention will become apparent from the following detailed description, taken in conjunction with the accompanying drawings, which illustrate, by way of example, the features of the present invention.

DETAILED DESCRIPTION OF THE PREFERRED EMBODIMENT

Larger individuals are often uncomfortable while seated on vehicles such as airplanes, buses or trains because their arms tend to extend over the armrests and contact adjacent passengers or passersby. As a result, many individuals have found it helpful to place their arms in a folded position across their chest. This position effectively narrows their body width and helps to avoid contact with others. Unfortunately, however, this position can be very difficult to maintain, particularly during longer trips. Therefore, a need exists for a garment system that provides users with the ability to releasably secure their hands or arms at selectable locations along their upper body. Such a device would help prevent muscle strain and thereby significantly increase the user's comfort during travel. Such a device would also be useful in a wide variety of other applications, such as for maintaining a user's hands or arms in a fixed position during rehabilitation after an injury or to help control body tremors resulting from neurological disorders. To be practical, the garment system must be reliable, convenient and easy to transport.

Figure 1:
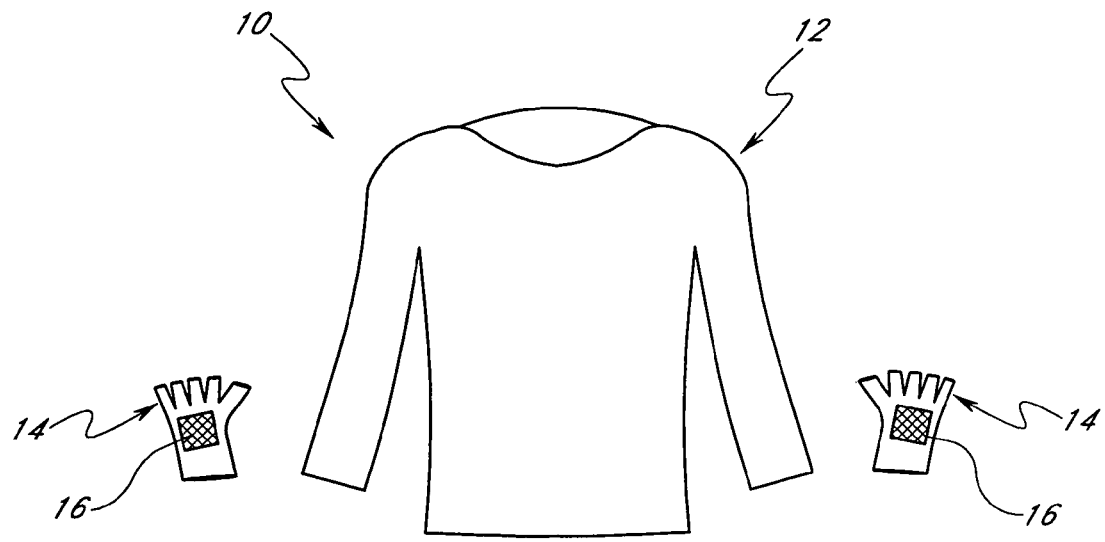
FIG. 1 is a perspective view of the garment according to a preferred embodiment of the present invention.
Figure 2:
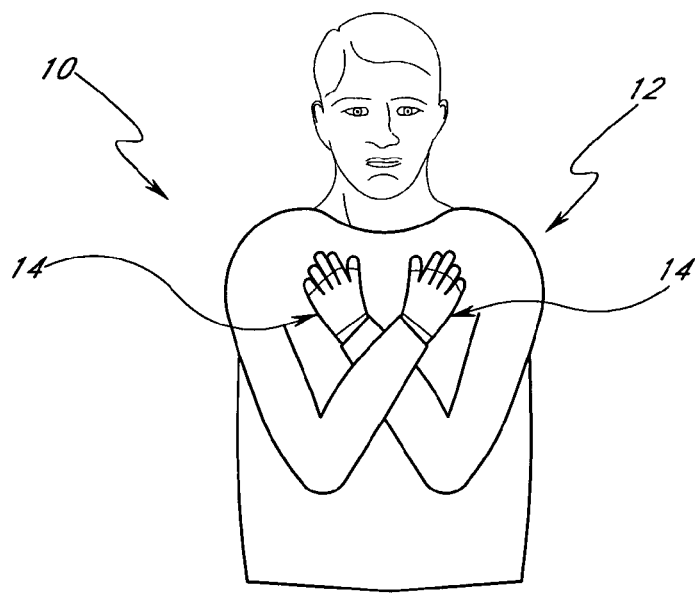
FIG. 2 is a perspective view illustrating the garment of FIG. 1 during use.

To address these needs, the present invention provides a new and improved garment adapted for providing users with the ability to releasably secure their hands or arms along their upper body. Referring now to FIGS. 1–2, for purposes of illustration, a preferred embodiment of the present invention provides a garment 10 including, generally, an upper portion 12 and a pair of hand portions 14. The upper portion 12 is worn over the torso and can take a variety of different forms, such as, for example, a shirt, a vest or a sweater. The upper portion 12 is preferably made of a material that provides a first attachment means, such as, for example, a loop material. Alternatively, patches of material can be sewn or otherwise attached to the upper portion of the garment to provide first attachment means in specific locations.

The hand portions 14 preferably comprise a pair of gloves with open fingers for comfort and convenience. However, it will be appreciated that the hand portions may take a variety of different forms. Furthermore, the hand portions may be worn on the wrists or forearms and therefore the term "hand portions" should not be construed as limited to articles adapted for wear only on the hands. The hand portions 14 include at least a region of material, such as, for example, a hook material, that provides a second attachment means. In the illustrated embodiment, each of the hand portions 14 is provided with a region of material 16 along the palm. The second attachment means releasably adheres to the first attachment means for providing the user with the ability to affix at least one hand to his or her upper body at a selectable location.

FIG. 2 illustrates the embodiment of FIG. 1 during use wherein the garment 10 provides a comfortable and convenient means for maintaining the user's hands in a fixed position along his or her upper body. As discussed above, this garment is particularly well suited for larger people while traveling on vehicles, such as on airplanes, buses, or trains, wherein the seats are often too narrow for their body size. By enabling the user to easily maintain his or her arms in a desired position along his or her upper body, the user's arms are prevented from contacting adjacent passengers or passersby and therefore the user can relax or sleep in comfort.

Still referring to FIG. 2, when the user places his or her palms against his or her upper body in the desired location, the region of material 16 along the palm of each of the hand portions 14 removably adheres to the material on the upper portion 12. Thus, the user can relax his or her shoulders and arms and permit the garment to bear the load of the dead weight of the arms. As a result, muscle strain and tendonitis in the arms and shoulders can be avoided. The first and second attachment means are chosen to be sufficiently strong such that the dead weight of the arms will not cause the first and second attachment means to separate disadvantageously. As discussed below, this garment can take many different forms; however, each of the forms is manufactured to be capable of providing the user with a reliable means to support of one or both arms.

Figure 3:
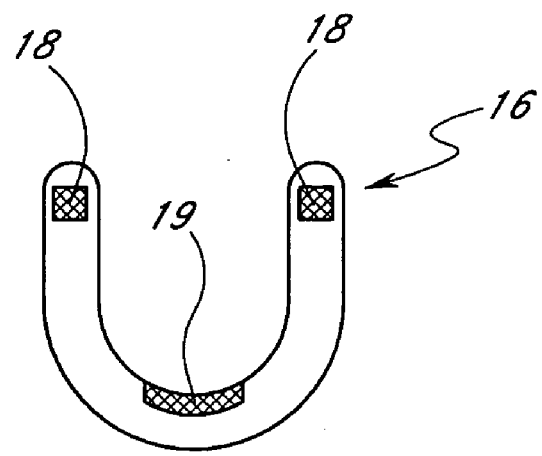
FIG. 3 is a perspective view of a neck pad adapted for attachment to the upper portion of the garment of FIG. 1 for improved head and neck support.
Figure 4:
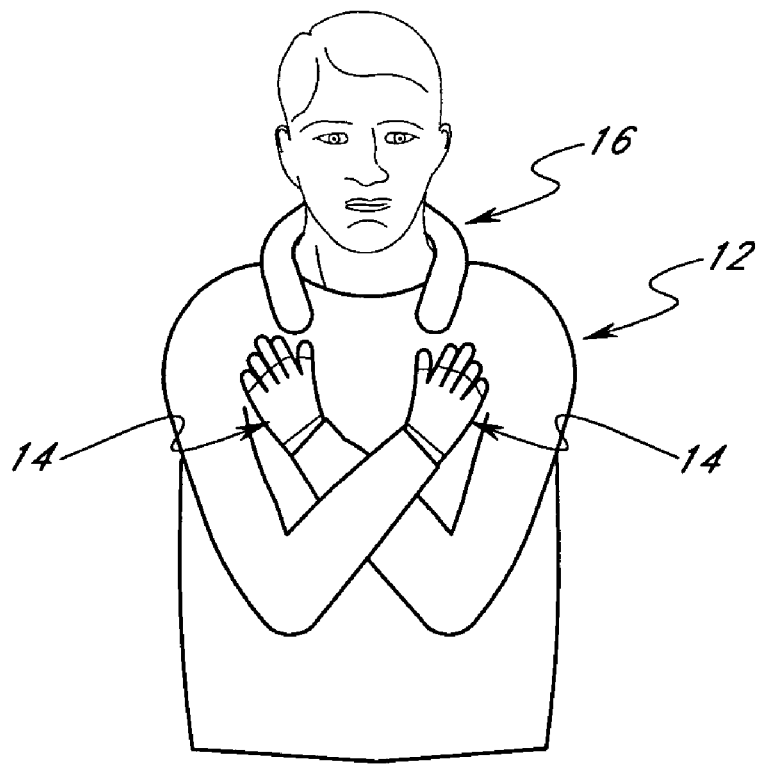
FIG. 4 is a perspective view illustrating the neck pad of FIG. 3 during use.

Additional components may be attached to the upper portion 12 of the garment 10 of FIG. 1. For example, as illustrated in FIG. 3, a neck pad 16 may be provided for enhanced head and neck support. The neck pad 16 is preferably provided with at least a region 18 of second attachment means, as illustrated in FIG. 3, for adhering to the upper portion 12 along the front shoulder region. The neck pad 16 can include an additional region 19 of second attachment means for attachment along the back of the user's collar on the upper portion 12. The neck pad may take a variety of forms, such as, for example, a stuffed pillow or an inflatable tube. FIG. 4 illustrates the neck pad 16 of FIG. 3 during use. In addition, similar pads may be attached to other areas of the upper portion 12 of the garment, such as, for example, along the forearms, elbows or on a shoulder, for enhancing the user's comfort. Furthermore, pockets (not shown) may be attached to the upper portion at selectable locations for a wide variety of different purposes.

Figure 5:
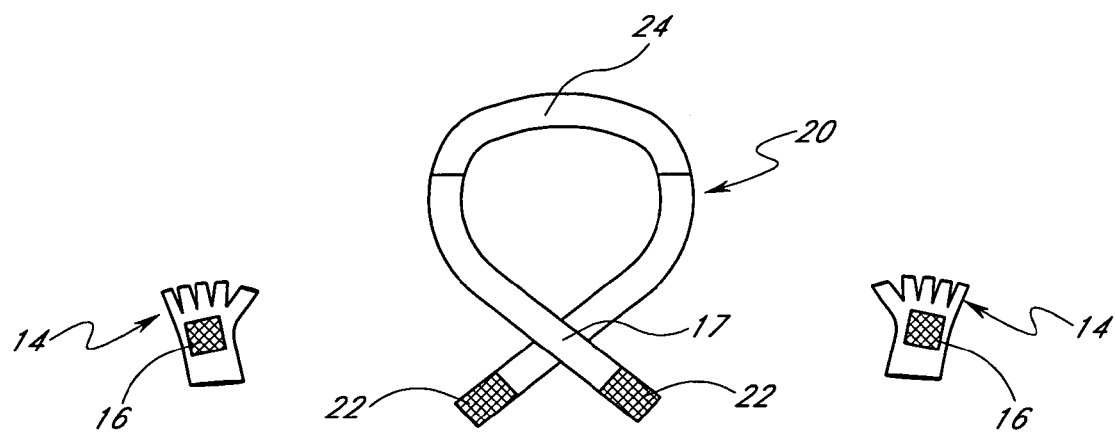
FIG. 5 is a perspective view of an alternative embodiment of the garment wherein the upper portion comprises a crossing strap that is worn around the neck.
Figure 6:
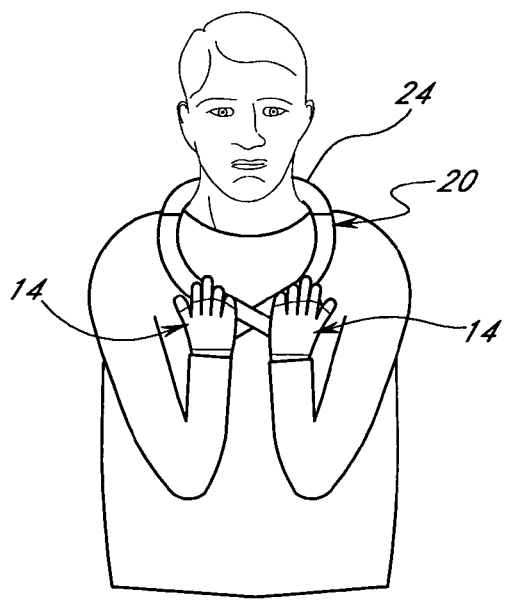
FIG. 6 is a perspective view illustrating the crossing strap of FIG. 5 during use.

FIG. 5 illustrates an alternative embodiment of a garment according to the present invention wherein the upper portion comprises a crossing strap 20. The crossing strap 20 preferably attaches to itself at attachment location 17 to form a loop. The loop of the crossing strap 20 is placed over the head and is provided with first attachment means at least along the strap ends 22. A significant feature of this embodiment is the ability to take the crossing strap 20 on and off quickly and easily, as compared with a sweater or vest. The crossing strap 20 illustrated in FIG. 5 may include a padded neck region 24 for enhanced head and neck support. Hand portions 14 similar to the gloves illustrated in FIGS. 1 and 2 may be used with the crossing strap 20, as illustrated during use in FIG. 6.

Figure 7:
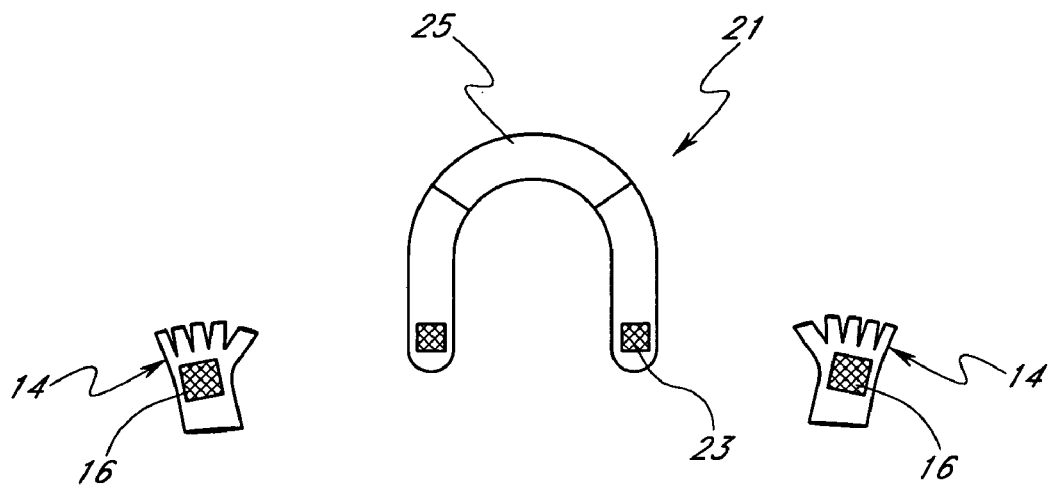
FIG. 7 is a perspective view of another alternative embodiment of the garment wherein the upper portion comprises a strap that wraps around the neck.
Figure 8:
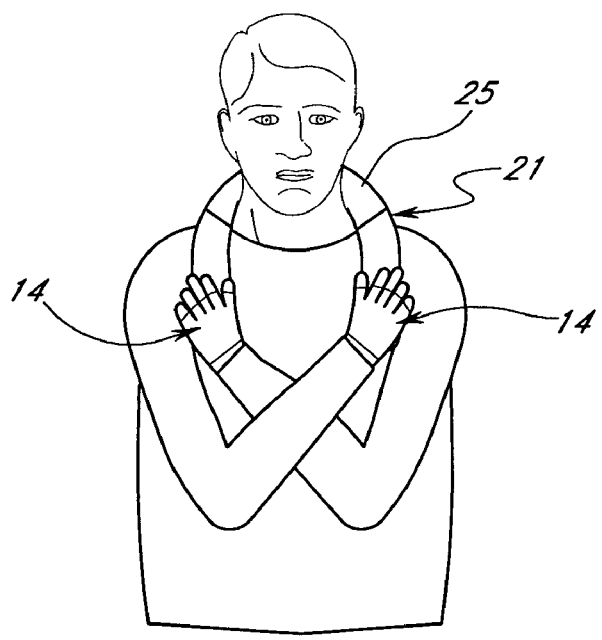
FIG. 8 is a perspective view illustrating the strap of FIG. 7 during use.

FIG. 7 illustrates another embodiment of a garment according the to present invention wherein the upper portion is provided in the form of a non-crossing strap 21. The strap 21 is placed around the back of the neck and lays over the front region of the shoulders. The strap 21 is provided with a first attachment means at least along the strap ends 23. The strap 21 illustrated in FIG. 7 also includes a padded neck region 25 for enhanced head and neck support. Hand portions 14 similar to the gloves illustrated in FIGS. 1 and 2 may be used with the strap 21, as illustrated during use in FIG. 8.

Figure 9:
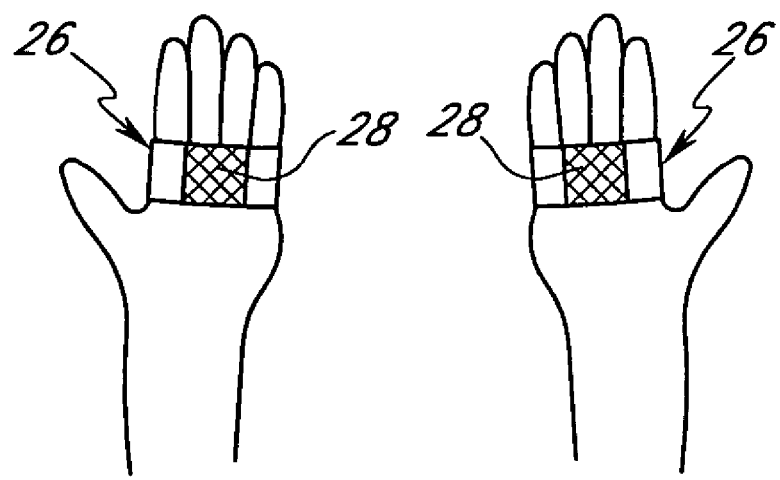
FIG. 9 is a top view of another alternative embodiment of the garment wherein the hand portions comprise a pair of hand straps.
Figure 10:
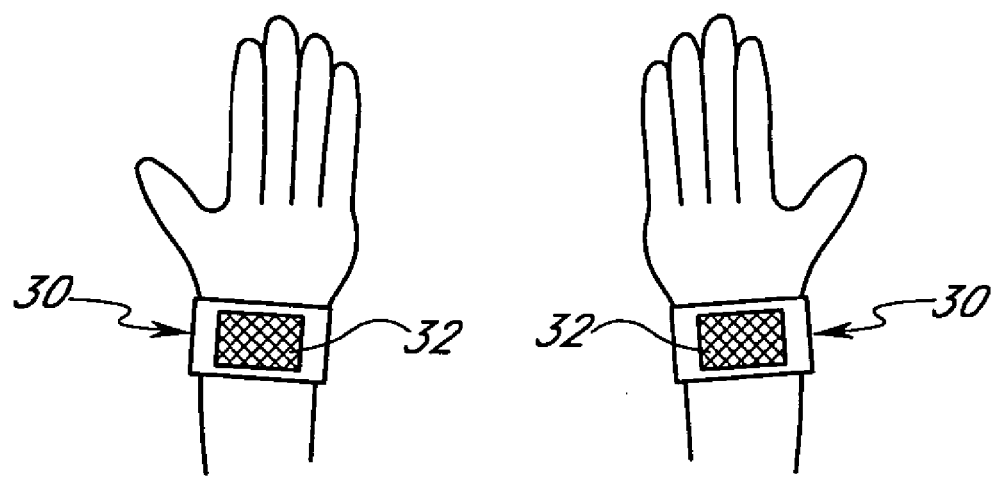
FIG. 10 is a top view of another alternative embodiment of the garment wherein the hand portions comprise a pair of wrist straps.

FIGS. 9 and 10 illustrate alternative embodiments of hand portions comprising straps that are worn around the hands or wrists. FIG. 9 illustrates an embodiment of the hand portions comprising palm straps 26 that wrap around the palm region of the hand. Each palm strap 26 includes an attachment region 28 provided with a second attachment means. FIG. 10 illustrates an embodiment of the hand portions comprising wrist straps 30. Each wrist strap 30 includes an attachment region 32 provided with a second attachment means.

Figure 11:
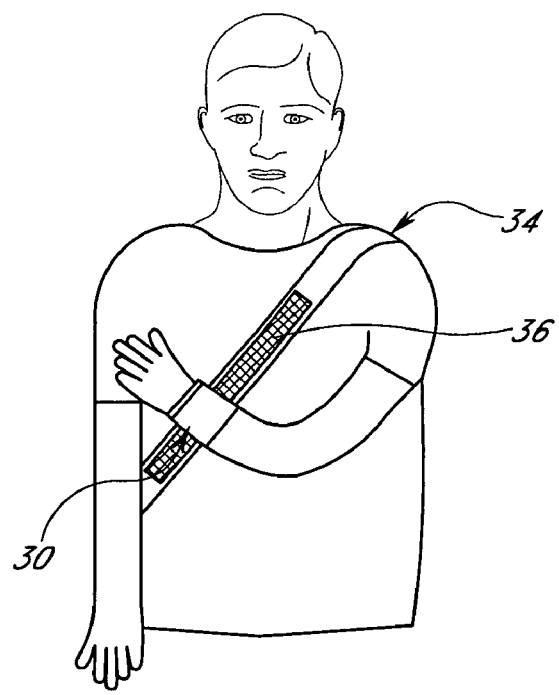
FIG. 11 is a perspective view of another alternative embodiment of the garment wherein the upper portion comprises a shoulder strap.

FIG. 11 illustrates yet another embodiment of the garment that is particularly well suited for immobilizing a victim's arm, such as, during rehabilitation after an injury. In the embodiment illustrated in FIG. 11, the upper portion of the garment comprises a shoulder strap 34 adapted for wear across one shoulder. A region of first attachment means is provided at least along a region 36 on the exterior of the shoulder strap 34. During use, the user wears a hand portion, such as one of the wrist straps 30 illustrated in FIG. 10, provided with a second attachment means adapted to releasably attach to the first attachment means 36 of the shoulder strap 34 at a selectable location.

Figure 12:
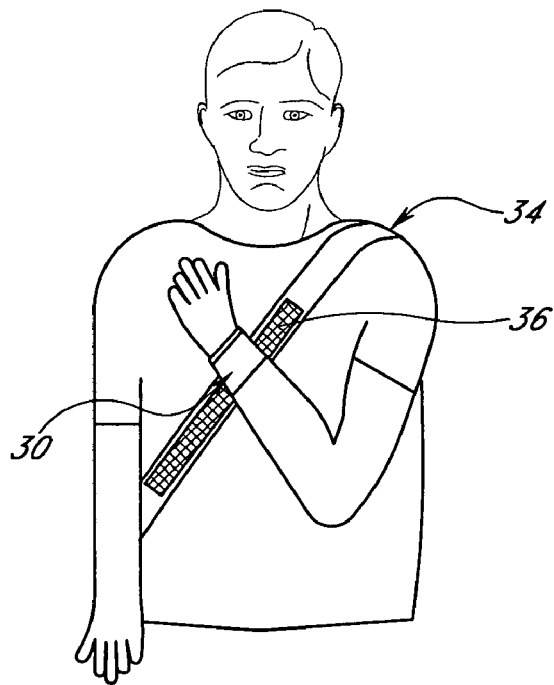
FIG. 12 is perspective view of the embodiment of FIG. 11 wherein the hand portion of the garment is attached to the shoulder strap in a different location.

The embodiment illustrated in FIG. 11 is particularly advantageous for applications wherein a sling may be impractical or cumbersome. This embodiment also advantageously allows the user to quickly and easily detach the wrist strap 30 from the shoulder strap 34 and thereby free the injured arm when necessary. In contrast, it is much more difficult to remove a conventional sling and then replace the arm in the sling when finished. A significant feature of this embodiment is the ability to select the attachment position of the arm according to the particular needs of the user. To illustrate this feature, FIG. 12 shows the embodiment of FIG. 11 during use, but with a wrist strap 30 attached to the shoulder strap 34 at a different location.

Figure 13:
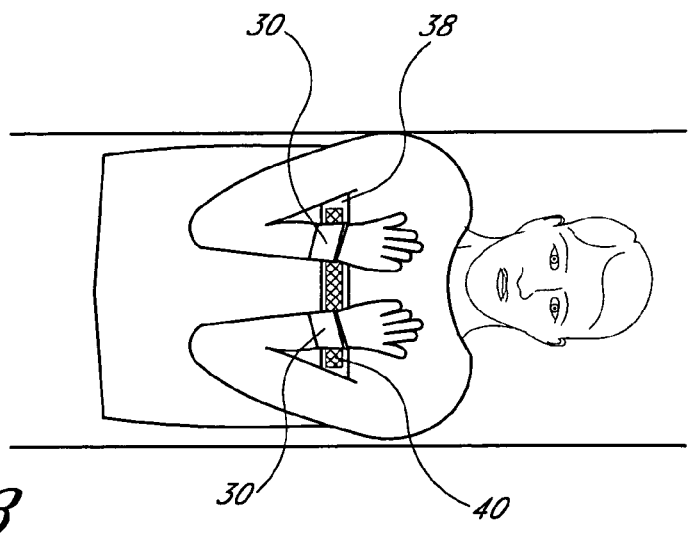
FIG. 13 is a top view of another alternative embodiment of the garment wherein the upper portion comprises a chest strap.

FIG. 13 illustrates yet another alternative embodiment that is particularly well-suited for use in maintaining a user's hands or arms in a fixed location while laying on a stretcher or cot. In this embodiment, the upper portion of the garment comprises a chest strap 38 adapted for wear around the user's chest. A region of first attachment means is provided at least along a region 40 on the front exterior of the chest strap 38. Hand portions, such as the wrist straps 30 shown in FIG. 10, provide second attachment means for releasable attachment to the chest strap 38. The combination of the wrist straps 30 and the chest strap 38 provides the ability to affix the user's hands or arms along his or her upper body in a quick and easy manner.

Figure 14:
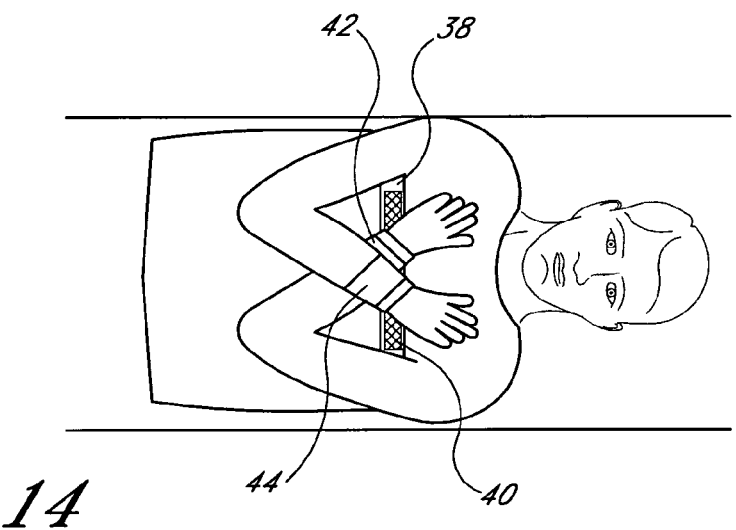
FIG. 14 is a top view of another alternative embodiment of the garment similar to the embodiment of FIG. 13 but wherein the wrist straps are adapted to attach to each other.

FIG. 14 illustrates yet another alternative embodiment wherein wrist straps 42, 44 are provided with attachment means on both the top and bottom sides. Using the wrist straps 42, 44 in combination with the chest strap 38, a first wrist strap 42 may be attached to the chest strap 38 while a second wrist strap 44 is attached to the first wrist strap 42.

Figure 15:
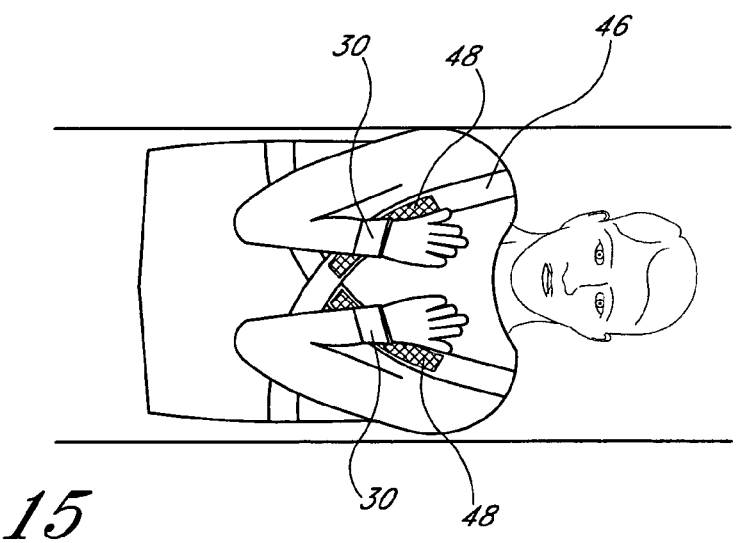
FIG. 15 is a top view of another alternative embodiment of the garment wherein the upper portion comprises a harness.

FIG. 15 illustrates yet another alternative embodiment wherein the upper portion of the garment comprises a harness 46 adapted for wear along the user's torso. This embodiment provides an upper portion that can be snugly fitted to the user. The harness 46 includes second attachment means 48 along the front exterior.

In each of the embodiments described above, the upper portion is adapted for wear along the torso region of the body is provided with a first attachment means, such as a durable fabric comprising a loop material. As discussed above, the upper portion may be manufactured in a variety of different forms including, but not limited to, a shirt, sweater, vest or strap. Furthermore, the upper portion may be manufactured to be very durable for long-term use or may be manufactured to be disposable, such as for one-time use by passengers on an airplane, train or bus.

The entire upper portion may be made of a loop material fabric or, alternatively, the fabric may be provided along only a limited desired region. In addition, the upper portion may have loop material along one or both sides (i.e., it may be single or double-sided). An upper portion manufactured from a double-sided loop material may be reversible and may also provide the ability to attach articles, such as pockets, along both the exterior and interior of the upper portion. The upper portion may also include a zipper in the front, preferably made of a plastic material for increased comfort and for avoiding detection by metal detectors.

The fabric used in the manufacture of the upper portion is preferably breathable, lightweight, washable, flame-retardant, waterproof and has a soft surface for comfort against the skin. In one preferred embodiment, the fabric comprises a laminated loop material such as VELTEX® manufactured by VELCRO USA, Inc. VELTEX® provides a relatively soft and even surface that is aesthetically pleasing and can be manufactured into a functional garment that can be worn for warmth or style in nearly any environment. In another preferred embodiment, the loop material comprises a medical grade laminate that provides increased attachment strength and improved duty cycles for durability over long periods. Medical grade laminates generally comprise a soft breathable foam substrate with knitted nylon loop provided along one or both surfaces thereof. VELCRO USA, Inc. provides a wide variety of medical grade laminates that are suitable for use with the present invention.

The hand portions of the garment are preferably manufactured to include a region of hook material, at least along the palm or inner wrist, for providing a second attachment means for attachment with the first attachment means. As discussed above, the hand portions may be manufactured for wear along the hands, wrists or forearms. The gloves may be open-fingered for increased comfort and functionality, similar to weight lifting gloves (e.g., as illustrated in FIG. 1).

Although the first and second attachment means of the preferred embodiments are described above with respect to hook and loop materials, it will be appreciated that alternative first and second attachment means may also be used. For example, the invention may be used with attachment devices such as buttons, hooks, snaps and clasps or any other device wherein the first attachment means may be releasably attached to a second attachment means in a quick and easy manner. Furthermore, it will be appreciated that, when hook and loop materials are used, the hooks may be provided on the upper portion while the loops are provided on the hand portions, or vice versa.

From the foregoing, it will be appreciated that the garment system of the present invention is very convenient to use. Due to the minimal number of components and ease of use, the garment may be easily transported or stored in small area. In addition, the garment system of the present invention is very versatile and can be used in a broad range of applications at home or during travel.

In certain applications, the garment system is usable by two or more persons. For example, in one application, the upper portion (e.g., a vest) is worn by a motorcycle rider while the hand portion (e.g., gloves) is worn by a passenger. In this application, the garment provides a safety mechanism by helping to ensure that the passenger's hands are firmly secured to the rider's upper body. In other applications, the upper portion and hand portions may be used for instructional purposes, such as hand placement during dancing, or for a wide variety of other instructional or recreational purposes, such as games and the like.

While particular forms of the invention have been illustrated and described, it will also be appreciated that various additional modifications can also be made without departing from the spirit and scope of the invention.

What is claimed is:

1. A method for preventing muscle strain by selectively attaching both of a user's hands at substantially fixed locations along the upper body comprising the steps of:
    providing a garment having an upper torso portion having a first attachment material;
    positioning the garment onto the upper body of the user;
    providing left and right hand portions, each of the hand portions having a second attachment material configured to be releasably engageable with the first attachment material and disposed at least along a palm side thereof;
    positioning the left and right hand portions on the user's left and right hands; and
    positioning the second attachment material on each of the left and right hand portions on the first attachment material of the upper torso portion so that the hands positioned within the left and right hand portions are substantially fixed along the upper torso portion of said garment for preventing muscle strain.

2. The method of claim 1, wherein the first attachment material includes a loop material and the second attachment material includes a hook material.

3. The method of claim 1, wherein the first attachment material includes a hook material and the second attachment material includes a loop material.

4. The method of claim 1, wherein the garment is a vest.

5. The method of claim 1, wherein the garment is a sweater.

6. The method of claim 1, wherein the first and second hand portions comprise first and second gloves.

7. The method of claim 6, wherein the second attachment material is sewn onto the palm side of the first and second gloves.

8. The method of claim 1, wherein the garment is a strap for wear around the user's upper body.

9. The method of claim 1, wherein the garment is a shoulder strap for wear across a shoulder and the first attachment material is located on an exterior portion of the strap for attachment to the second attachment material.

10. The method of claim 1, wherein the garment further comprises a neck pad that is releasably securable to the upper torso portion for supporting the user's head during rest.

11. The method of claim 8, wherein the strap is formed with a padded neck portion.

* * * * *